(12) United States Patent
Wayman et al.

(10) Patent No.: US 8,189,197 B2
(45) Date of Patent: May 29, 2012

(54) OPTICAL SENSOR FOR CHARACTERIZING A SUBSTRATE

(75) Inventors: William H Wayman, Ontario, NY (US); Chu-Heng Liu, Penfield, NY (US); James R Beachner, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 414 days.

(21) Appl. No.: 12/566,711

(22) Filed: Sep. 25, 2009

(65) Prior Publication Data

US 2011/0075131 A1    Mar. 31, 2011

(51) Int. Cl.
*G01N 21/84* (2006.01)
*G01N 21/00* (2006.01)
(52) U.S. Cl. .................. 356/429; 356/432; 356/433
(58) Field of Classification Search ........... 356/429–433
See application file for complete search history.

(56) References Cited

U.S. PATENT DOCUMENTS

| | | | | |
|---|---|---|---|---|
| 4,837,614 | A * | 6/1989 | Omi | 358/512 |
| 2005/0073544 | A1* | 4/2005 | Scofield et al. | 347/16 |
| 2005/0083530 | A1* | 4/2005 | Ogihara et al. | 356/446 |
| 2005/0122358 | A1* | 6/2005 | Mitsuzawa | 347/14 |
| 2007/0002326 | A1* | 1/2007 | Doak et al. | 356/446 |

OTHER PUBLICATIONS

U.S. Appl. No. 12/266,125; filed Nov. 6, 2008; Wayman et al.; titled "Substrate Characterization Device and Method for Characterizing a Substrate," assigned to the same assignee as the present invention.

* cited by examiner

*Primary Examiner* — Michael P Stafira

(57) ABSTRACT

A substrate characterization device is provided which includes an optical sensor module and a processor. The optical sensor module includes a light emitting source and a light receiving detector for communicating with the substrate and providing an indication of the diffusion of light through the substrate. The indication of the diffusion of light through the substrate is a signal provided to a processor in communication with a memory module for making a comparison of the signal generated by the optical sensor module with a reference signal to determine the quality of the substrate.

12 Claims, 5 Drawing Sheets

OPTICAL SENSOR FOR CHARACTERIZING A SUBSTRATE

BACKGROUND

The present disclosure relates to substrate sensing devices, and more particularly, to an optical device and method for characterizing a substrate.

It is well known that the quality of a substrate, such as paper, can vary from batch to batch, which can have a significant impact on image quality ("IQ") performance of print jobs. This variation usually occurs when paper is manufactured. Even substrates of the same type, whether they are glossy, recycled, copy, or formal substrates, may vary in quality from batch to batch. One of the types of variations in which batches may differ is their electrical properties. It is known that the electrical properties of a substrate play a major role in image quality performance, since an electric field is utilized to transfer toner to substrate. Thus, the electrical properties affect the IQ performance of a print job, which in turn, increases image mottle and/or spots, more specifically, half-tone mottle.

In the business arena, a customer usually reports a print quality problem to a service technician. The service technician then examines the configuration of a printing machine, the condition and quality of the imaging components of the printing machine, and the type and/or brand of paper being used. The service technician evaluates the problem and presents the results to the customer. It would be useful and beneficial to have a device that can characterize the quality of paper and determine whether the substrate has caused or will cause any deterioration in print quality and/or image quality.

It is known in the prior art, particularly, in pending patent application reference: U.S. patent application Ser. No. 12/266,125; filed Nov. 6, 2008; Wayman et al.; titled "Substrate Characterization Device and Method For Characterizing a Substrate," now U.S. Pat. No. 7,855,565, issued Dec. 21, 2010, assigned to the same assignee as the present invention, to use electrical capacitance measurements to identify paper image quality. However, there are limitations on the use and versatility of this type of measurement. Under certain conditions, the optical properties of the substrates, rather than the electrical properties can affect the image quality in a more significant way. It has been discovered that optical measurement techniques provide favorable/complementary options to define paper quality and image quality in a printing system.

SUMMARY

In embodiments of the present disclosure, a substrate characterization device includes an optical sensor module and a processor. The optical sensor module, for example, could be a fiber optic pair or any variation of lenses and mirrors to reflect light from an image medium and record the variations of the diffusion or travel of the light through the medium to represent the quality of the medium. In general, an optical sensor communicates with the substrate (e.g., paper) and measures the variability of the diffusion of light by the substrate to generate a signal indicative of the measured variance.

The processor is in operative communication with a memory module and configured to execute a series of programmable instructions for making a comparison of the signal generated by the optical sensor module with at least one reference signal. The processor is further configured to generate at least one characterization signal based on the comparison. This characterization signal is indicative of at least one characteristic (e.g., quality) of the substrate. This one reference signal may be stored by the memory module or may be a real-time reference signal. In addition, the characteristic may be clarity, resolution, sharpness, or transparency.

In some embodiments, a measuring module is in communication with the probe and configured to measure a distance along the substrate. The distance may be measured via a line-scan by moving the probe along the substrate and/or by moving the substrate in relation to the probe. In some embodiments, the substrate characterization device is integrated within a xerographic printer and/or a handheld device.

In other embodiments, a substrate handling device includes a substrate transport mechanism, a substrate transport controller, and a substrate characterization device. The substrate transport mechanism is configured to transport a substrate in response to a control signal. The substrate transport controller is in operative communication with the substrate transport mechanism. The substrate characterization device is similar to the substrate characterization device described above. The substrate transport controller is configured to generate the control signal in response to the at least one characterization signal.

In other embodiments, a method for characterizing a substrate includes: positioning a substrate; measuring a variance in the diffusion of light through a given range or distance within the substrate; generating a signal indicative of the measured variance; comparing the signal generated with at least one stored reference signal; and generating at least one characterization signal indicative of at least one characteristic of the substrate. The method may performed by a xerographic printer or a handheld device.

In other embodiments, a substrate characterization device includes an optical sensor module, a memory module, and a processor. The optical sensor module generates a signal and the processor is configured to execute a series of programmable instructions for comparing the signal generated by the sensor module with a reference signal stored by the memory module and generates at least one characterization signal. The characterization signal is indicative of at least one characteristic of the substrate. In particular, the at least one characteristic is an optical characteristic of the substrate.

DETAILED DESCRIPTION

Figure 1:
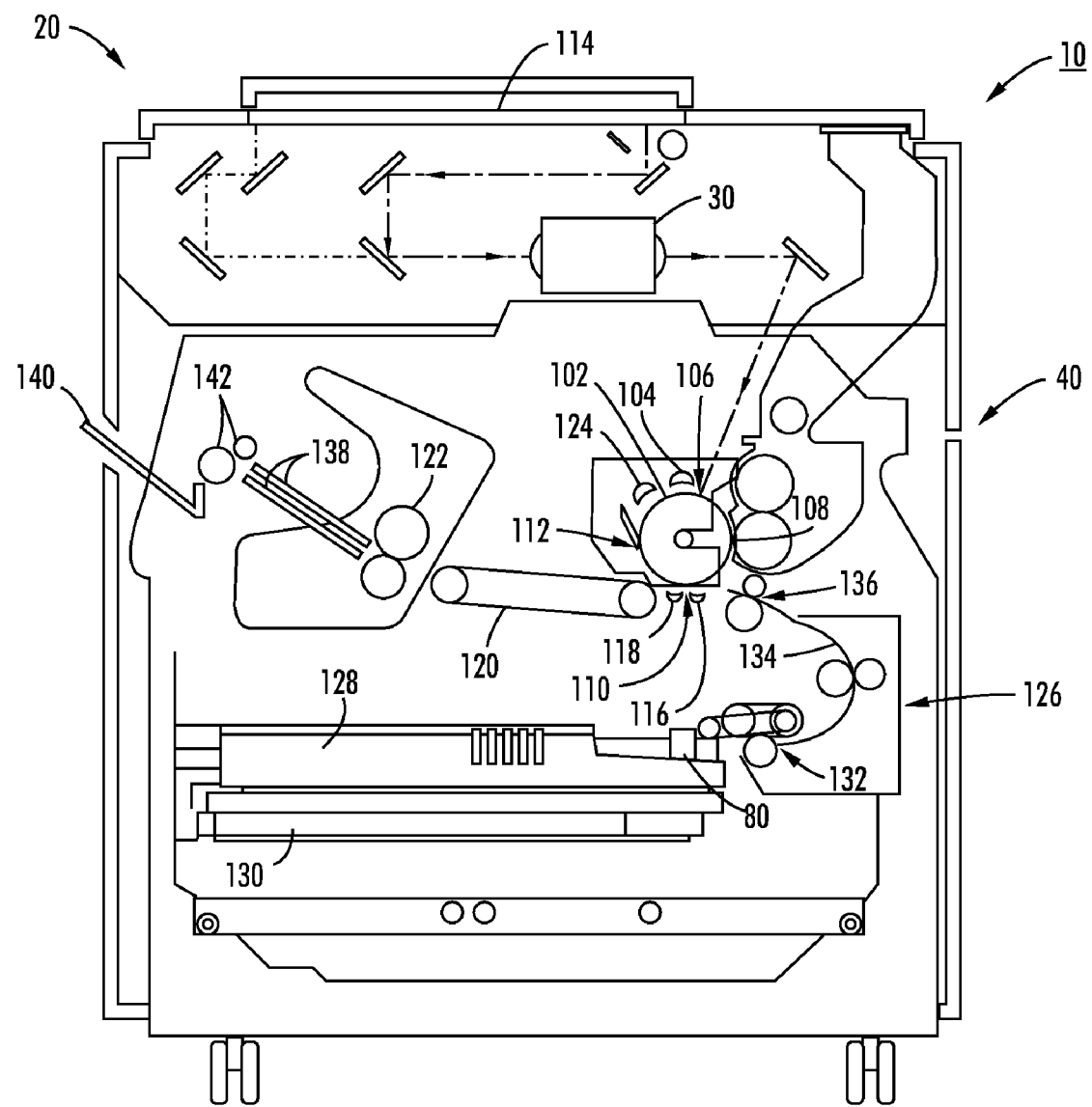
FIG. 1 shows a partial, side-elevational view of an exemplary networked electrophotographic machine incorporating a substrate characterization device according to an embodiment of the present disclosure.

Embodiments of the presently disclosed substrate characterization system and method will now be described in detail with reference to the drawings in which like reference numerals designate identical or corresponding elements in each of the several views.

Referring initially to FIG. 1, a partial, cutaway, side-elevational view of an exemplary multifunction electrostatographic machine 10 is shown. The machine 10 includes an image capture system 20, a controller 30, and a printing system 40. The printing system 40 includes a photoreceptor drum 102 mounted for rotation (as shown in FIG. 1) to carry a photoconductive imaging surface of the drum 102 sequentially through a series of processing stations. Namely, a charging station 104, an imaging station 106, a development station 108, a transfer station 110, and a cleaning station 112.

The general operation of the printing system 40 begins by depositing a uniform electrostatic charge on the photoreceptor drum 102 at the charging station 104 such as by using a corotron. An image of a document to be reproduced that is positioned on a platen 114 is obtained by the image capture system 20. In this embodiment, the image capture device within the image capture system 20 is a scanning device that produces a flowing light image that is directed to a controller 30. The controller 30 digitizes the flowing light image and/or passes the light image to the drum 102 at the imaging station 106 in the event that a physical copy of the document is to be made. The flowing light image selectively discharges the electrostatic charge on the photoreceptor drum 102 in the image of the document, whereby an electrostatic latent image of the document is laid down on the drum 102.

At the development station 108, the electrostatic latent image is developed into visible form by depositing toner particles on the charged areas of the photoreceptor drum 102. Cut sheets of a substrate are moved into the transfer station 110 in synchronous relation with the latent image on the drum 102 and the developed image is transferred to the substrate at the transfer station 110. A transfer corotron 116 provides an electric field to assist in the transfer of the toner particles to the substrate. The substrate is then stripped from the drum 102, the detachment being assisted by the electric field provided by an alternating current de-tack corotron 118. The substrate carrying the transferred toner image is then carried by a transport belt system 120 to a fusing station 122.

After transfer of the toner image from the drum 102, some toner particles usually remain on the drum 102. The remaining toner particles are removed at the cleaning station 112. After cleaning, any electrostatic charges remaining on the drum are removed by an alternating current erase corotron 124. The photoreceptor drum 102 is then ready to be charged again by the charging station 104, as the first step in the next copy cycle.

The transport of the substrate to the transfer station 110 in the above process is accomplished by a substrate supply system 126. In this embodiment, the substrate is selected from one of two types of substrate stored in two substrate trays, an upper, main tray 128 and a lower, auxiliary tray 130. The top sheet of substrate in the selected tray is brought, as required, into feeding engagement with a common, fixed position, sheet separator/feeder 132. The sheet separator/feeder 132 feeds a substrate around a curved guide 134 for registration at a registration point 136. Before the substrate is registered, the substrate is transported through, or by, a substrate characterization device 80, such that the substrate is characterized (discussed below). Once registered, the substrate is fed into contact with the drum 102 in synchronous relation to the toner image so as to receive the toner image on the drum 102 at the transfer station 110.

The substrate carrying the transferred toner image is transported, by the transport belt system 120, to the fusing station 122, which is a heated roll fuser. The heat and pressure in the nip region between the two rolls of the fuser cause the toner particles to melt and some of the toner is forced into the fibers or pores of the substrate. The substrate with the fused image which is a copy of the document is then fed by the rolls in the fusing station 122 along output guides 138 into a catch tray 140 via the output roll pair 142.

Figure 2A:
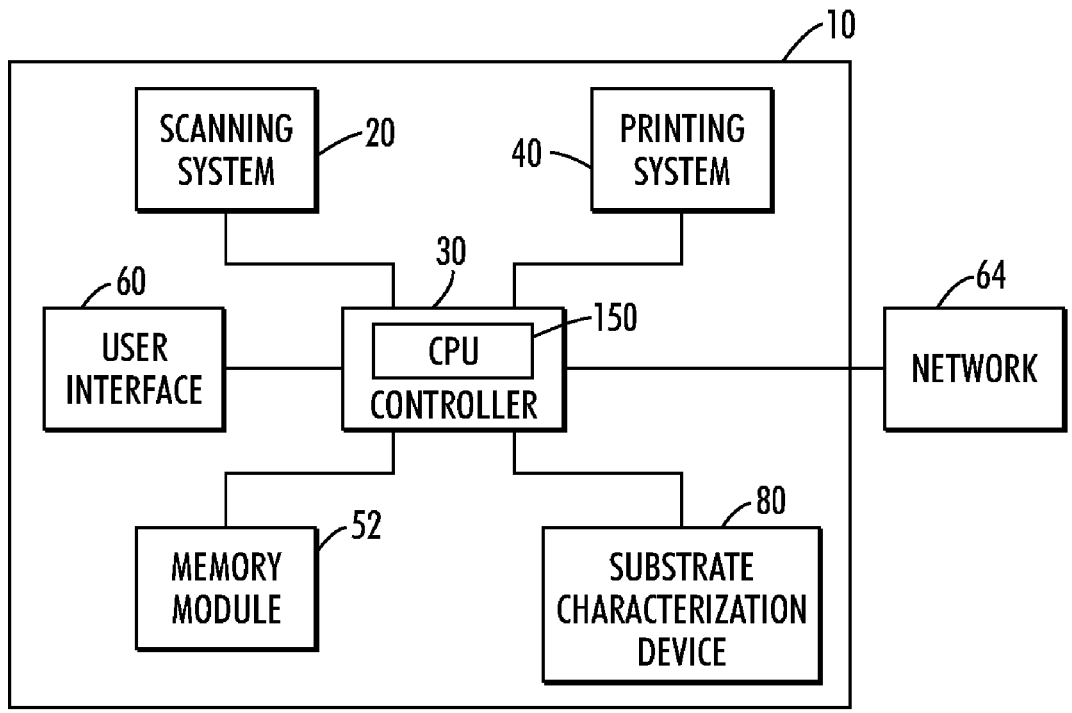
FIG. 2A shows a schematic representation of a digital processing station having a substrate characterization device within the electrophotographic machine of FIG. 1.

Operation of the machine 10 is controlled by the controller 30 shown in FIG. 2A. The controller 30 includes a CPU or processor 150 and communicates with a memory module 52. The memory module 52 may comprise RAM, ROM, CD-ROM, or other media of storage such as hard disk, magnetic tape, or the like. Other devices for accepting, capturing and storing data are well known and the above list should not be construed as exhaustive.

The memory module 52 may contain stored document files 54 and system software 56. The system software 56 which is run by the processor 50 may reside in ROM, RAM, or other units of storage. It will also be appreciated that the memory 52 may be a shared or distributed resource among many processors in a networked configuration.

The controller 30 is connected to the image capture scanning system 20, the printing system 40, a user interface 60, a substrate characterization device 80 and a network 64. The image capture device in this embodiment is a scanning device; however, other image capture devices may be used including, but not limited to, charge coupling devices. The user interface 60 is generically labeled and encompasses a wide variety of such devices. These interface devices include touch screens, keyboards, and graphic user interfaces.

In embodiments, the substrate characterization device 80 (FIGS. 2A and 2B) may be placed in the printing device to directly characterize a substrate as it enters or is fed into the machine 10, for example, but not limited to, at a location placed directly next to the upper, main tray 128. In another embodiment, the substrate characterization device 80, as described above, can be placed just before or just after the upper, main tray 128 and/or the lower, auxiliary tray 130. However, the substrate characterization device 80 can render characterizations of substrate at any location of the printing machine 10.

In embodiments, as shown by example in FIG. 2A, the substrate characterization device 80 can provide feedback to the processor 50 for taking action in response to critical substrate measurements, such as the projection of light onto a substrate surface and detecting the diffusion of the light within the substrate as manifested by the detection of the light reflected from the substrate surface and recorded at a suitable photo detector. Additionally, there may be provided any number of substrate characterization devices placed anywhere in the printer as needed, not only in the locations illustrated or discussed.

The information gathered therefrom is used by the processor 50 and/or any other processor/controller within the printing machine, in various ways (e.g., executing a series of programmable instructions) to aid in the operation of the printer, whether in a real-time feedback loop, an offline calibration process, a registration system, etc. While the substrate characterization device 80 and the processor 50 are shown in the figures as being separate elements, it can be appreciated that in other embodiments, the substrate characterization device 80 may be a part of the processor 50.

In embodiments, the substrate characterization device 80 is configured to measure different kinds and amounts of substrate, for example, substrate batches. The substrate characterization device may also rank and/or characterize different batches of substrate for image quality (IQ) performance. A so-called "high quality" substrate batch could be saved for the highest IQ jobs, where a so-called "lower quality" batch could be used for average IQ jobs. IQ performance may be, for example, but is not limited to, clarity, resolution, sharpness, and transparency.

In general, a substrate characterization device 80 is an optical system based upon the projection of light onto a medium and detecting the reflected light from the medium by a light detector. Substrate 82 may be, for example, but not limited to, a sheet of paper, glossy paper, recycled paper or any other kind of substrate known in the art, including non-paper substrates such as plastic substrates.

Figure 2B:
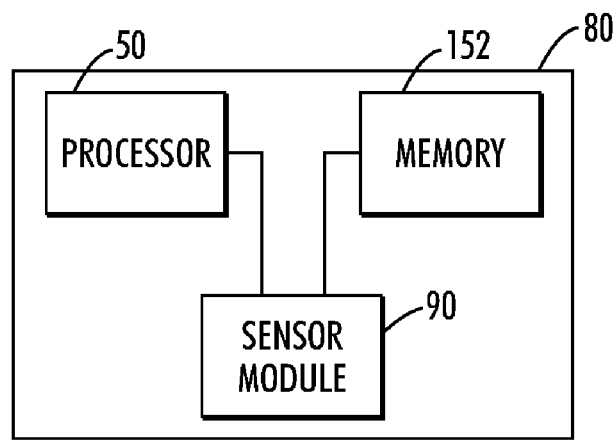
FIG. 2B shows a schematic representation of an exemplary embodiment of the components of the substrate characterization device of FIG. 2A.
Figure 3:
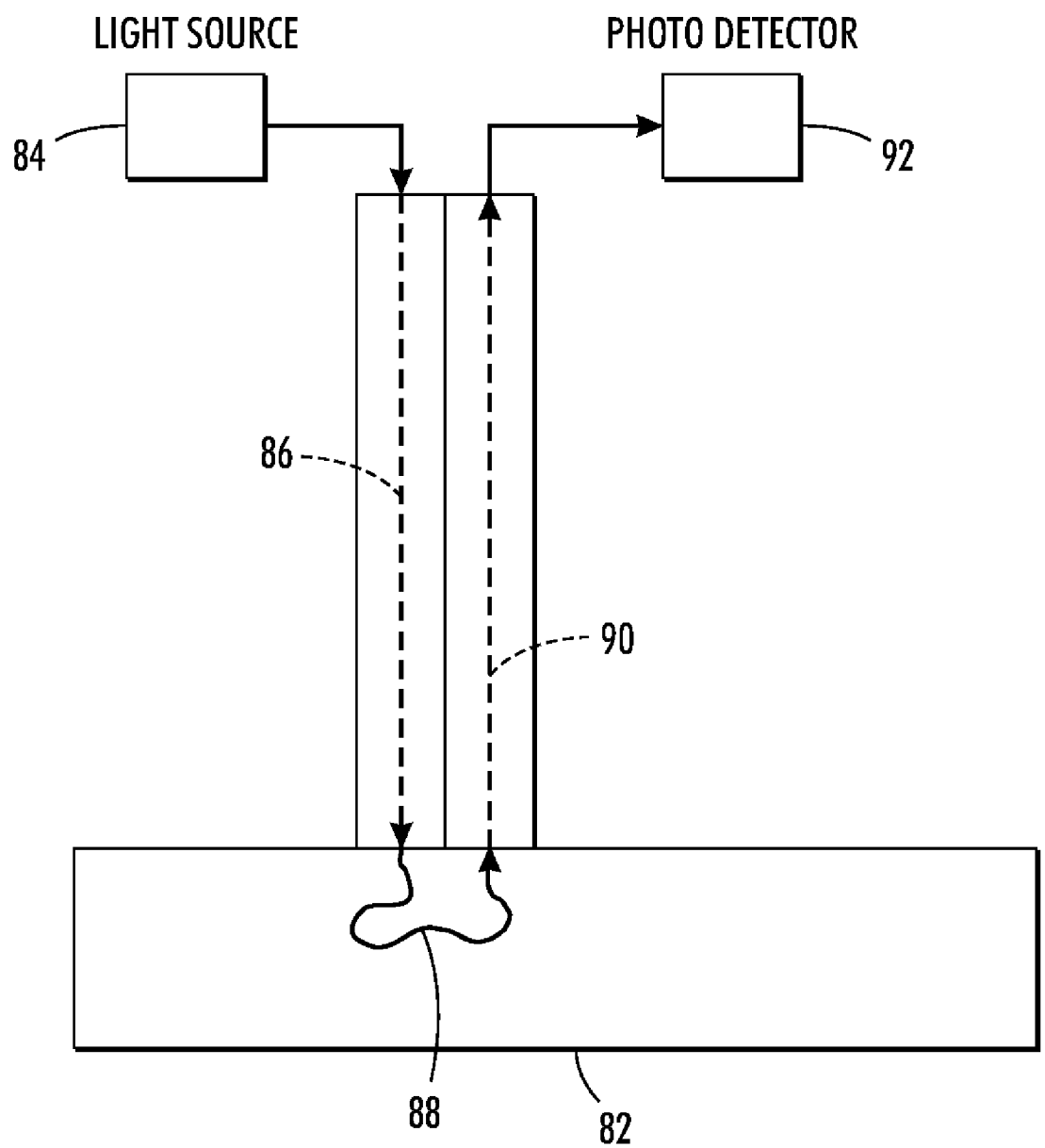
FIG. 3 shows an exemplary fiber optic sensor for use in the substrate characterization device of FIG. 2A.

Referring now to FIG. 3, there is illustrated a sensor module 90 of substrate characterization device 80 (shown in FIGS. 2A and 2B), in particular, a medium optical crosstalk paper optical quality sensor based on the uniformity of the paper optical diffusion. In particular, the sensor or probe is constructed of a light source 84, photo detector 92, two parallel optical fibers 86, 90, and measures the amount of light that diffused laterally within the substrate along paths as illustrated at 88. It should be noted that most of the light reflected from a typical substrate such as paper is not directly reflected from the paper surface. Instead, most of the light enters the bulk of the substrate and gets randomly scattered around. For a white substrate, most of the scattered light finds a way out of the substrate after multiple scatterings before being absorbed. In physics terms, this random scattering process is described as light diffusion. One characteristic of this invention is that the sampling spot is distinctly away from the illumination spot. Therefore, direct reflection is being avoided and measured signal is purely caused by light diffusion. The size of the optical fibers and the separation between them are optimized to sample a range of diffusion lengths. Preferably the optical fibers are approximately 1 mm diameter. The optical diffusion pattern 88 depending upon the diffusion of light through the medium as shown provides a representative signal that is detected by the photo detector. This representative signal is then compared to a reference signal or signals stored in memory, to indicate the type or quality of the medium.

It should be noted that two dimensional scanning techniques were used to generate image maps or signals of different papers or medium to provide reference signals or maps to compare with the signals of the medium currently in use for printing. In particular, various paper types were scanned to establish a quality index with related scanned signal representations. The scanned signal representations provide comparison signals for reference to scanned signals. For example, a synthetic substrate can serve as the best quality reference while different grades of regular papers can define the quality scales.

In operation, the paper is placed in relation to the probe and the paper or probe is then translated to generate a line scan of the fiber optic crosstalk uniformity. This crosstalk can be described as light entering the paper with a fraction of the light being absorbed and a fraction being reflected and exiting the paper. It has been found that for a given paper type, the variation in this reflected signal is well correlated with the paper image quality performance.

Consider a sheet of paper uniformly covered with perfect halftone dots. It is well known that halftone dots suffer optical dot gain due to light diffusion inside the paper. The halftone dots partially block the incident light hitting the paper. Now consider the light hitting the uncovered areas between the dots. This light will not be completely reflected even for perfectly white paper. The light will enter the paper through the white space, diffusing within the paper and re-surface again. Some fraction will re-surface under the halftone dot and be absorbed and the other fraction will re-emerge from the un-covered area and exit the paper. Only the light that enters and emerges from the uncovered area contributes to the brightness of the halftone shade. This brightness as seen by an observer is strongly modulated by the characteristics of the light diffusion within the paper. It is the variability in diffusion in the 1-3 mm dimension that will contribute to image mottle. In practice, it should be noted that a single line scan of sufficient length, or multiple shorter line scans may be sufficient to measure paper IQ performance.

In operation, the reflectance or diffusion signals produced by the scan of the medium are then analyzed by an analysis module (e.g., a processor 50), which characterizes the substrate 82 by comparing the resulting signal to a reference signal stored in a memory module 152 (as shown in FIG. 2B). The reference signal may be a real-time reference signal or a predetermined reference signal (e.g., look-up table and stored values).

Figure 4:
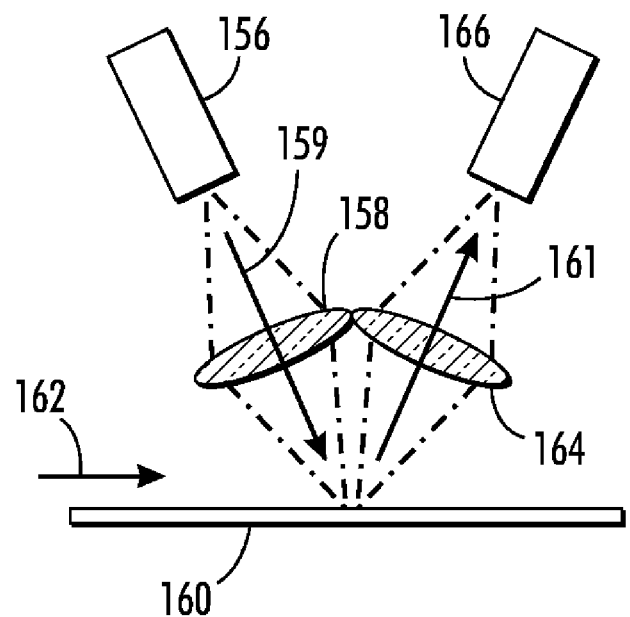
FIG. 4 shows an exemplary light lens optical sensor using focusing lenses for use in the substrate characterization device of FIG. 2A.

With reference to FIG. 4, there is illustrated another embodiment of an optical sensor module 90. For example, a suitable light source such as an LED is shown at 156. Light source 156 projects a ray of light, illustrated by arrow 159, through light lens 158. Light lens 158 focuses the light onto the paper 160. Light is reflected from paper 160 as illustrated by the arrow 161 and lens 164 focuses the reflected light 161 to a suitable photo detector such as photodiode 166. It should be noted that arrow 162 implies relative movement of the paper 160 and optical sensor module 90. Either the medium or the sensor module could be stationary while the other moves accordingly, to generate scan line data, or both the sensor module and the medium could be moving to generate two-dimensional scan line data. It should also be noted that the illuminated light area of the medium indicated by arrow 159 is generally adjacent to the detected light area of the medium indicated by arrow 161 and preferably, these areas do not overlap. In contrast to a conventional probe that measures the color or density, this invention measures the diffusion properties of the substrate. The unique feature of this probe is that the illumination spot (the focused image of the source through lens 158) is distinctly away from the sampling spot (the focused image of the detector through lens 164).

Figure 5:
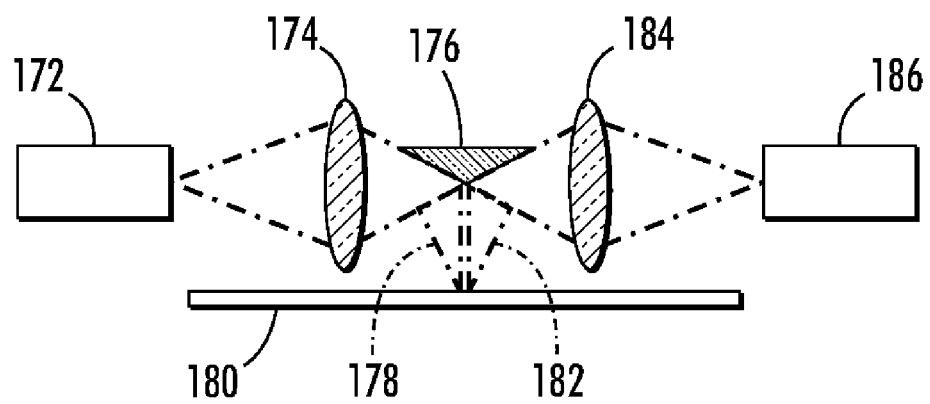
FIG. 5 shows an exemplary optical sensor using focusing lenses and a double mirror for use in the substrate characterization device of FIG. 2A.

With reference to FIG. 5, there is shown another embodiment of an optical sensor. In particular, a suitable light source 172 projects a ray of light through lens 174 and the ray of light is focused by lens 174 onto a double mirror 176. The double mirror 176 redirects the light ray to the paper 180 as illustrated at 178. The light is then reflected from the paper 180 to the double mirror 176 and the double mirror 176 reflects the light to the lens 184. The lens 184 focuses the light to a suitable photo detector 186.

Figure 6:
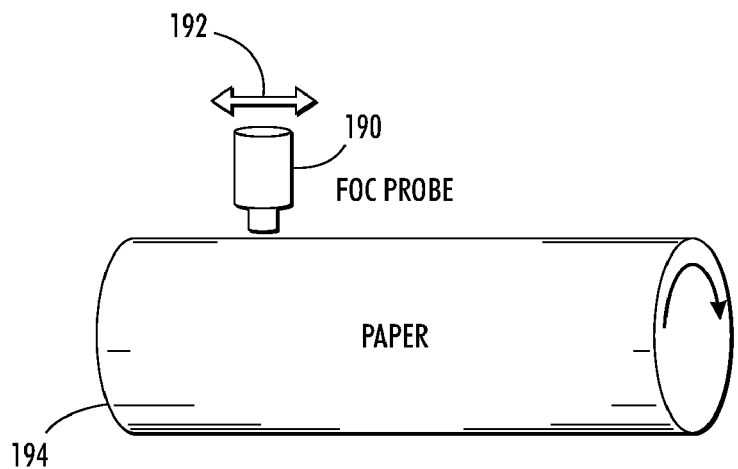
FIG. 6 illustrates a 2-dimensional optical probe for use in the substrate characterization device of FIG. 2A.

The substrate characterization device, in accordance to the present disclosure, was capable of characterizing the quality of every sheet of substrate by a single pass of single or multiple line-scans. Thus, a sensor module, as described above, can be implemented as an inline device (e.g., in a printing device or a sheet handling device), along the substrate path before transfer, the substrate characteristics can be operably communicated to a processor for IQ adjustments or other programmable instructions. An example of this type of device is illustrated in reference to FIG. 6. In particular, FIG. 6 illustrates a basic sensor module or probe 190 for lateral movement back and forth in the direction of arrow 192 across a medium illustrated at 194. With the paper rotating in the direction of rotation of a drum as illustrated by arrow 'y', there is illustrated a scanning operation in two-dimension. In embodiments, "low quality" substrates may be rejected and stored in a separate bin for low IQ print jobs and/or "high quality" substrates may be stored in a separate bin for high IQ print jobs.

In other embodiments, the substrate characterization device, in accordance to the present disclosure, may be used by a service technician to determine if a customer's substrate is the root cause of a printer malfunction, for example, an IQ problem. In embodiments, the substrate characterization device, in accordance to the present disclosure, can be in the form of a handheld device, where a service technician can carry the handheld substrate characterization device and perform a line-scan to determine whether the substrate and/or the batch of substrate is the cause of a printing IQ problem.

In other embodiments, a substrate characterization device, in accordance to the present disclosure, may be used as a substrate inspection tool for incoming substrate qualification. In addition, the substrate characterization device can be configured to be coupled to a substrate manufacturing process. A substrate manufacturing device is generally known in the art. The process of making substrate will not be discussed, since the present embodiment can be operably coupled to any substrate manufacturing device.

Figure 7:
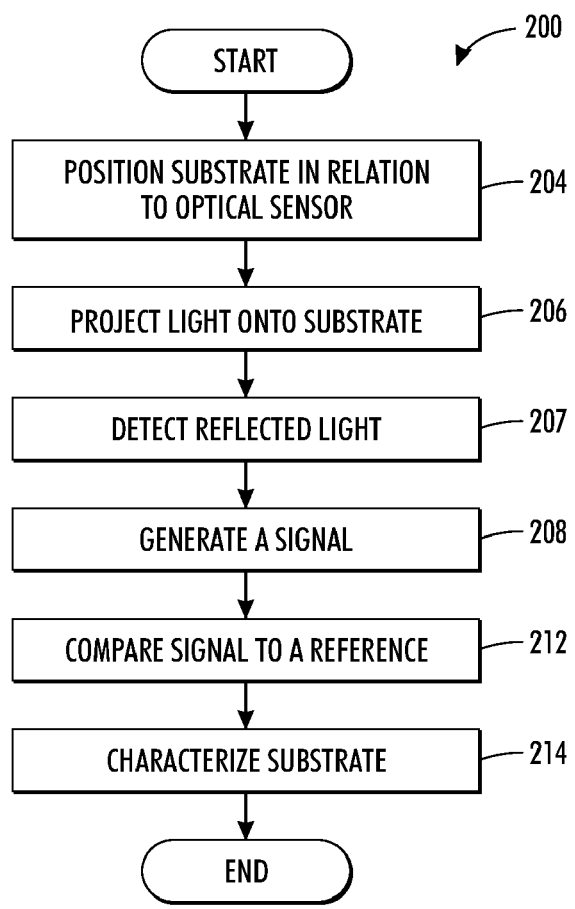
FIG. 7 shows a flow chart of a method for characterizing a substrate in accordance with an embodiment of the present disclosure.

In accordance with the present disclosure, a method for characterizing a substrate is disclosed. The method for characterizing a substrate, as shown in FIG. 7, is generally depicted as reference numeral 200. In an initial step, a substrate, for example, but not limited to, a sheet of paper is provided to a substrate characterization device 80, as discussed above.

In step 204, a substrate is positioned in relation to an optical sensor module such that light can be projected onto the substrate and reflected light can received by a suitable photo detector.

In step 206, light is projected from the optical sensor module onto the substrate, and in step 207 reflected light from the substrate is received by the photo detector. It should be noted that in step 207 a portion of the light received by the photo detector is light that is diffused within the substrate.

In step 208, a signal is generated by the photo detector in response to the reception of deflected light from the substrate for comparison with suitable reference signals stored in memory.

In step 212, the generated signal is compared with the reference signals in memory and in step 214, the substrate is characterized based on the comparison of the generated signal and the reference signals.

The result is that the characteristic or quality of the substrate is determined based on the comparison. In other embodiments, an additional step is executed by the processor 50 in accordance with the determined characteristic of the substrate. As discussed above, "high quality" substrates may be stored for high IQ print jobs, and "low quality" substrates may be stored for low IQ print jobs. In addition, a so-called "high quality" substrate batch is characterized for the highest IQ jobs, where a so-called "lower quality" batch is characterized for average IQ jobs. IQ performance may be, for example, but is not limited to, clarity, resolution, sharpness, and transparency.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A substrate handling device comprising:
    a substrate transport mechanism configured to transport a substrate in response to a control signal;
    a substrate transport controller in communication with said substrate transport mechanism; and
    a substrate characterization device including:
    an optical sensor module including a light emitting source and a light receiving detector for communicating with said substrate, said sensor module enabled to measure the diffusion of light through said substrate, the diffusion of light through the substrate generating a signal, said signal indicating paper optical quality based on the uniformity of the paper optical diffusion; and
    a processor in communication with a memory module for executing a series of programmable instructions for making a comparison of said signal generated by said sensor module with at least one reference signal, said processor generating at least one characterization signal based on said comparison.

2. The substrate handling device of claim 1 wherein the optical sensor module is a combination light source, light detector, and parallel fiber optic pair.

3. A method for characterizing a substrate comprising the steps of:
    positioning a substrate in relation to a light source and photo detector, the light source projecting light onto a surface of the substrate;
    detecting by the photo detector a portion of the light, projected by the light source, a portion of the light projected by the light source being diffused within the substrate;
    generating a signal indicative of the light diffused within the substrate;
    comparing said signal generated with at least one stored reference signal; and
    generating a characterization signal indicative of at least one characteristic of said substrate.

4. The method of claim 3 including the step of measuring a distance along said substrate.

5. The method of claim 3 wherein said at least one characteristic of said substrate is based on a quality of said substrate.

6. A substrate characterization device comprising:
    an optical sensor module in operative communication with a substrate, the optical sensor module including a light source and a photo detector for generating a signal in reference to the substrate;
    the optical sensor module further including a light projecting fiber optic and a light receiving fiber optic for measuring the amount of light diffused within the substrate along a path, the entry point to the path being the connecting point of the light projecting fiber optic with the substrate and the exit point of the path being the connecting point of the light receiving fiber optic with the substrate, the connecting point of the light projecting fiber optic being distinct from the connecting point of the light receiving fiber optic;
    a memory module for storing a reference signal; and
    a processor in operative communication with the memory module for comparing the signal generated by the optical sensor module with the reference signal and generating a characterization signal based on the comparison.

7. The substrate handling device of claim 1 wherein the light source projecting light onto a surface of the substrate, projects light on the surface at a first point, and the photo detector detecting a portion of the diffused light within the substrate, detects the diffused light at a second point on the substrate surface, the first and second points on the surface of the substrate are separate and connected by the path of the diffused light through the substrate.

8. The substrate handling device of claim 2 wherein the parallel fiber optic pair includes a first fiber optic connected to the substrate at a first point for projecting light onto the substrate and a second fiber optic connected to the substrate at a second point for receiving light diffused through the substrate, the first point being distinct from the second point and including an arbitrary path of diffused light within the substrate linking the first point and the second point.

9. The substrate handling device of claim 8 wherein the optical fibers are approximately 1 mm diameter.

10. The substrate handling device of claim 8 wherein the optical fibers sample a range of lengths of diffused light within the substrate.

11. The method of claim 3 wherein said signal indicates paper optical quality based on the uniformity of the paper optical diffusion.

12. The method of claim 3 wherein the light source projecting light onto a surface of the substrate, projects light on the surface at a first point, and the photo detector detecting a portion of the diffused light within the substrate, detects the diffused light at a second point on the substrate surface, the first and second points on the surface of the substrate are separate and connected by the path of the diffused light through the substrate.

* * * * *